United States Patent [19]

Reinehr et al.

[11] Patent Number: 4,658,066
[45] Date of Patent: Apr. 14, 1987

[54] 1,10-SUBSTITUTED 1,11-DIAMINO-UNDECA-3,7-DIENES AND PROCESSES FOR THEIR PREPARATION

[75] Inventors: Dieter Reinehr, Kandren, Fed. Rep. of Germany; Josef Pfeifer, Therwil, Switzerland

[73] Assignee: Ciba-Geigy Corporation, Ardsley, N.Y.

[21] Appl. No.: 763,321

[22] Filed: Aug. 7, 1985

Related U.S. Application Data

[63] Continuation of Ser. No. 461,044, Jan. 26, 1983.

[30] Foreign Application Priority Data

Jan. 29, 1982 [CH] Switzerland .................... 560/82

[51] Int. Cl.$^4$ .................... C07C 55/28; C07C 57/34
[52] U.S. Cl. .................... 564/490; 564/489; 564/509; 564/511
[58] Field of Search ............... 564/509, 489, 490, 511

[56] References Cited

U.S. PATENT DOCUMENTS 4,277,621  7/1981  Reinehr et al. .................... 564/265
4,355,177 10/1982  Reinehr et al. .................... 564/36

FOREIGN PATENT DOCUMENTS 11599  5/1980  European Pat. Off. .

OTHER PUBLICATIONS

Morrison and Boyd, "Organic Chemistry" 3rd ed. Allyn and Bacon, Boston 1973, pp. 734-735.

Primary Examiner—Charles F. Warren
Assistant Examiner—Elizabeth A. Flaherty
Attorney, Agent, or Firm—Harry Falber

[57] ABSTRACT

Novel diamines of the formula

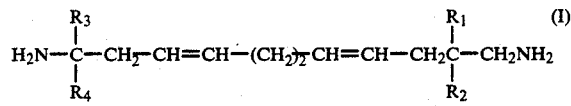

are described, in which $R_1$ is $C_{1-12}$-alkyl, $R_2$ is H or $C_{1-12}$-alkyl, $R_3$ is $C_{1-12}$-alkyl, cycloalkyl having 4–12 ring C atoms, $C_{7-8}$-aralkyl, substituted or unsubstituted aryl or, if $R_4$=H, is also —CH=CH—alkyl or —C(alkyl)=CH— alkyl each having 1–4 C atoms in the alkyl groups, and $R_4$ is H, $C_{1-12}$-alkyl, cycloalkyl having 4–12 rings C atoms, $C_{7-8}$-aralkyl or substituted or unsubstituted aryl, or $R_1$ and $R_2$ and/or $R_3$ and $R_4$ together are $C_{3-11}$-alkylene. The diamines (I) are valuable intermediates and are suitable especially for the preparation of transparent crosslinkable polyamides.

5 Claims, No Drawings

1,10-SUBSTITUTED 1,11-DIAMINO-UNDECA-3,7-DIENES AND PROCESSES FOR THEIR PREPARATION

This application is a continuation of application Ser. No. 461,044, filed Jan. 26, 1983.

The invention relates to novel 1,10-substituted 1,11-diamino-undeca-3,7-dienes and processes for their preparation. The novel 1,11-diamino-undeca-3,7-dienes are valuable intermediates, in particular as polycondensation components for the preparation of crosslinkable polyamides.

The novel 1,11-diamino-undeca-3,7-dienes are those of the formula I

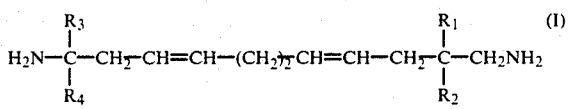

in which $R_1$ is alkyl having 1–12 C atoms, $R_2$ is hydrogen or alkyl having 1–12 C atoms, $R_3$ is alkyl having 1–12 C atoms, cycloalkyl having 4–12 ring C atoms, aralkyl having 7 or 8 C atoms, substituted or unsubstituted aryl or, if $R_4$ is hydrogen, is also —CH=CH—alkyl or —C(alkyl)=CH—alkyl, each having 1–4 C atoms in the alkyl groups, and $R_4$ is hydrogen, alkyl having 1–12 C atoms, cycloalkyl having 4–12 ring C atoms, aralkyl having 7 or 8 C atoms or substituted or unsubstituted aryl, or $R_1$ and $R_2$ and/or $R_3$ and $R_4$ together are alkylene having 3–11 C atoms.

Alkyl groups $R_1$ to $R_4$ can be straight-chain or branched. Alkyl groups $R_1$, $R_2$ and $R_4$ preferably have 1–5 C atoms and are straight-chain. Alkyl groups $R_3$ advantageously have 1–7 C atoms and especially 1–5 C atoms. Examples of alkyl groups $R_1$ to $R_4$ are: the methyl, ethyl, n-propyl, isopropyl, n-, sec.- and tert.-butyl, n-pentyl, 2-pentyl or 3-pentyl, n-hexyl, 2-heptyl or 3-heptyl, n-octyl, n-decyl and n-dodecyl groups.

If $R_3$ is a group —CH=CH—alkyl or —C(alkyl)=CH—alkyl, the alkyl groups in these substituents are preferably straight-chain and are especially methyl or ethyl.

Cycloalkyl groups $R_3$ and $R_4$ can be unsubstituted or substituted by $C_{1-4}$-alkyl groups. They are especially cycloalkyl substituted by a methyl or ethyl group. Preferably, however, cycloalkyl groups $R_3$ and $R_4$ are unsubstituted and have 5–8 ring C atoms. The cyclopentyl group and, in particular, the cyclohexyl group are particularly preferred.

Possible aralkyl groups $R_3$ and $R_4$ are, in particular, the benzyl, methylbenzyl or phenylethyl group. If $R_3$ or $R_4$ is substituted aryl, possible substituents are, in particular, alkyl groups having 1–4 and especially 1 or 2 C atoms. Aryl groups $R_3$ and $R_4$ can carry several alkyl groups, but are preferably substituted by only one alkyl group. Particular preference is given to the 1-naphthyl or 2-naphthyl group, phenyl substituted by an alkyl group having 1–4 and particularly 1 or 2 C atoms, and, very particularly, unsubstituted phenyl.

Alkylene groups represented by $R_1$ and $R_2$ and/or $R_3$ and $R_4$ together preferably have 4–7 C atoms. These are especially the tetramethylene group and, very particularly, the pentamethylene group.

Preferred compounds of the formula I are those in which $R_1$ is alkyl having 1–5 C atoms, $R_2$ is hydrogen or alkyl having 1–5 C atoms, or $R_1$ and $R_2$ together are alkylene having 4–7 C atoms, $R_3$ is alkyl having 1–7 C atoms, cycloalkyl having 5–8 C atoms, unsubstituted phenyl or, if $R_4$=H, is also —C(C$_2$H$_5$)—CHCH$_3$, and $R_4$ is hydrogen or alkyl having 1–5 C atoms. Particularly preferred compounds of the formula I are those in which $R_1$ is alkyl having 1–5 C atoms, $R_2$ is hydrogen or alkyl having 1–5 C atoms, or $R_1$ and $R_2$ together are alkylene having 4–7 C atoms, $R_3$ is alkyl having 1–5 C atoms, unsubstituted phenyl or, if $R_4$=H, is also —C(C$_2$H$_5$)=CHCH$_3$, and $R_4$ is hydrogen or methyl, and in particular those in which $R_1$ is methyl or ethyl, $R_2$ is hydrogen, methyl or ethyl, $R_3$ is alkyl having 1–5 C atoms or unsubstituted phenyl, and $R_4$ is hydrogen or methyl. The compound of the formula I in which $R_1$ and $R_2$ are methyl, $R_3$ is isopropyl and $R_4$ is hydrogen is very particularly preferred.

Examples of specific compounds of the formula I are: 2,2-dimethyl-11-methyl-1,11-diamino-undeca-4,8-diene, 2,2-dimethyl-11-ethyl-1,11-diamino-undeca-4,8-diene, 2,2-dimethyl-11-isopropyl-1,11-diamino-undeca-4,8-diene, 2,2-dimethyl-11-n-hexyl-1,11-diamino-undeca-4,8-diene, 2,2-dimethyl-11-phenyl-1,11-diamino-undeca-4,8-diene, 2,2-dimethyl-11-cyclohexyl-1,11-diamino-undeca-4,8-diene, 2,2-diethyl-11-isopropyl-1,11-diamino-undeca-4,8-diene, 2,2-diethyl-11-(3-pentyl)-1,11-diamino-undeca-4,8-diene, 2,2-dimethyl-11-pentamethylene-1,11-diamino-undeca-4,8-diene, 2,2-diethyl-11-phenyl-1,11-diamino-undeca-4,8-diene, 2-methyl-11-phenyl-1,11-diamino-undeca-4,8-diene, 2-methyl-2-n-propyl-11-(2-pentyl)-1,11-diamino-undeca-4,8-diene, 2-methyl-11-cyclohexyl-1,11-diamino-undeca-4,8-diene, 2-methyl-11-(3-pentyl)-1,11-diamino-undeca-4,8-diene, 2-ethyl-2-n-butyl-11-(3-heptyl)-1,11-diamino-undeca-4,8-diene, 2-ethyl-2-n-butyl-11-ethyl-1,11-diamino-undeca-4,8-diene, 2-ethyl-2-n-butyl-11-phenyl-1,11-diamino-undeca-4,8-diene, 2,11,11-trimethyl-1,11-diamino-undeca-4,8-diene, 2-pentamethylene-11-cyclohexyl-1,11-diamino-undeca-4,8-diene, 2-tetramethylene-11-cyclopentyl-1,11-diamino-undeca-4,8-diene and 2,2,11,11-tetramethyl-1,11-diamino-undeca-4,8-diene.

The compounds of the formula I can be obtained, for example, either by reducing compounds of the formula II

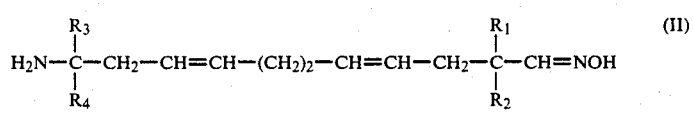

directly to give compounds of the formula I, or by first dehydrating the compounds of the formula II to give compounds of the formula III

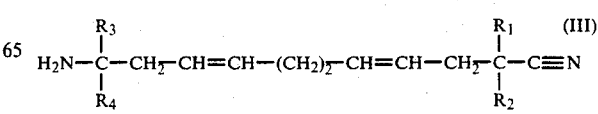

and then reducing the compounds of the formula III to give compounds of the formula I, $R_1$ and $R_4$ being as defined under the formula I.

The reduction of the compounds of the formula II or III to give compounds of the formula I can be carried out in a manner known per se, for example by means of Bouveault-Blanc reduction with sodium metal and alcohols, if appropriate in the presence of an inert organic solvent, for example aromatic hydrocarbons such as benzene, toluene or xylene. The preferred solvent is toluene.

The alcohols used in this process are advantageously alkanols having up to 6 C atoms, such as methanol, ethanol, propanol, isopropanol, butanols and hexanols. Isopropanol is preferred. The reaction temperatures for the reduction with sodium metal and alcohols are advantageously between 25° C. and the reflux temperature of the reaction mixture, preferably between 60° and 120° C.

The reduction can also be carried out with lithium aluminium hydride, if appropriate together with aluminium chloride, in an anhydrous, preferably organic medium, for example diethyl ether, tetrahydrofuran, benzene, toluene or n-hexane, advantageously at temperatures of between 0° and 80° C. Other suitable reducing agents are sodium borohydride, zinc dust or zinc in glacial acetic acid, or sodium amalgam in an acid medium. The two last-mentioned reducing agents are particularly suitable for the direct reduction of the oximes of the formula II. The reduction with sodium metal and alcohols in the presence of an inert organic solvent is preferred, the abovementioned preferences applying to the alcohol, the solvent and the reaction temperatures.

If appropriate, the dehydration of the compounds of the formula II to give compounds of the formula III can also be carried out chemically or thermally, in a manner known per se.

Examples of suitable dehydrating agents for chemical dehydration are anhydrides of aliphatic monocarboxylic acids having 2-5 C atoms and unsubstituted or substituted by halogen atoms or alkyl groups, such as acetic, propionic, butyric and valeric anhydrides and trichloroacetic, trifluoroacetic, trimethylacetic, triethylacetic and tri-n-butylacetic anhydrides; alkyl chloroformates having 1-5 C atoms, such as methyl, ethyl, isopropyl and isobutyl chloroformates; acetyl chloride, thionyl chloride, benzoyl chloride, benzenesulfonyl chloride, sulfuryl chloride, phosphorus pentoxide mixed with ethanol, phosphorus oxychloride, polyphosphoric acid and aqueous alkali, such as aqueous NaOH or KOH. The said dehydrating agents can, if appropriate, be used in a mixture with catalysts, for example alkaline earth metal or alkali metal salts of aromatic monocarboxylic acids or of aliphatic monocarboxylic acids having 1-3 C atoms, such as sodium benzoate, sodium salicylate, calcium and sodium formates, calcium, magnesium, sodium and potassium acetates and sodium propionate, or tertiary bases such as triethylamine, pyridine and dimethylaniline.

The preferred dehydrating agent is acetic anhydride. Chemical dehydration is advantageously carried out in the presence of an organic diluent or solvent which is inert under the reaction conditions. Examples of suitable diluents or solvents are aromatic hydrocarbons such as benzene and toluene, aromatic or aliphatic nitriles, particularly benzonitrile and alkylnitriles having 2-5 C atoms, such as acetonitrile, propionitrile and butyronitrile, and also anhydrous acetic acid. Preferred diluents or solvents are acetonitrile and, in particular, anhydrous acetic acid.

Chemical dehydration is generally carried out at temperatures of between 50° C. and the reflux temperature of the reaction mixture.

Thermal dehydration can be carried out, for example, over aluminium oxide or thorium oxide at temperatures of between 340° and 360° C. Chemical dehydration is preferred.

The starting materials of the formula II are known and can be prepared by the process described in European Pat. No. 11,599.

The diamines of the formula I are valuable intermediates and are applied, for example, as polycondensation components for the preparation of transparent crosslinkable polyamides. Such polyamides can be prepared, in a manner known per se, by the polycondensation of diamines of the formula I with saturated or unsaturated aliphatic and/or aromatic dicarboxylic acids or amide-forming derivatives thereof, preferably in the presence of an inorganic or organic phosphorus compound as an accelerator. They can be crosslinked thermally or photochemically, preferably in the presence of free-radical initiators. Photochemical crosslinking is advantageously carried out by means of polythiols having at least two thiol groups per molecule, in the presence of photosensitisers such as benzophenone, thioxanthone and the like. The said polyamides or their mixtures with polythiols and sensitisers are suitable, for example, for the production of solvent-resistant coatings on various materials, particularly metals, for the production of images under the action of light or for the production of transparent mouldings, for example by the injection-moulding or extrusion process. The transparent polyamides obtained using diamines of the formula I and aromatic and/or aliphatic dicarboxylic acids, particularly terephthalic acid, isophthalic acid and/or adipic acid, are distinguished by low water uptake, high resistance to hydrolysis and/or good dimensional stability under the action of moisture. Furthermore, they give very strongly adhering, solvent-resistant coatings and, in contrast to previously known, unsaturated polyamides, have a good compatibility with polythiols. By virtue of their good solubility in various organic solvents, they can also be readily crosslinked under the action of heat.

(A) PREPARATION EXAMPLES

EXAMPLE 1

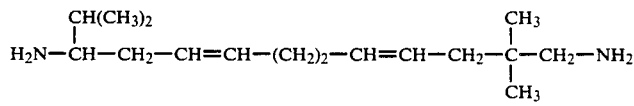

(a) 80 g (0.3 mol) of 2,2-dimethyl-11-isopropyl-11-amino-undeca-4,8-dienaldoxime are treated with 100 ml of glacial acetic acid, with stirring. HCl gas is then passed in up to saturation and 30.6 g (0.3 mol) of acetic anhydride are added dropwise in the course of 15 minutes. The reaction mixture is heated for a further 4 hours under reflux, the glacial acetic acid is distilled off and the residue is dissolved in water. After the solution has been rendered basic with sodium hydroxide solution, the organic phase which separates out is taken up in toluene and the mixture is distilled. This gives 68.5 g (0.276 mol) of 1,1-dimethyl-10-isopropyl-10-amino-deca-3,7-diene-nitrile, corresponding to a yield of 92% of theory; boiling point: 94° C./3 Pa.

$^1$H NMR spectrum: $\tau$(ppm): 4.5 (m), 7.45 (quin), 7.9 (m), 2.0–2.5 (m), 8.65 (s), 8.84 (s), 9.07 (dd) in the ratio 4:1:8:1:6:2:6.

(b) 23 g (1 mol) of sodium are added to 150 ml of toluene and the mixture is heated until the sodium melts. The source of heat is then removed and the mixture is stirred until the sodium is finely divided as a grey dispersion. A solution of 53 g (0.214 mol) of 1,1-dimethyl-10-isopropyl-10-amino-deca-3,7-diene-nitrile in 100 ml of isopropanol is then added dropwise to this mixture. The resulting mixture is boiled under reflux for a further 3 hours and treated with 200 ml of water, and the organic phase is separated off. After the solvent has been distilled off, 44 g (0.175 mol) of 2,2-dimethyl-11-isopropyl-1,11-diamino-undeca-4,8-diene are obtained, corresponding to a yield of 81.5% of theory; boiling point: 86° C./ Pa; $n_D^{20}$=1.4810.

Analysis for $C_{16}H_{32}N_2$ (molecular weight: 252.45): calculated: C, 76.12%; H, 12.78%; N, 11.10%. found: C, 75.59%; H, 12.97%; N, 10.82%.

$^1$H NMR spectrum: $\tau$(ppm): 4.6 (m), 7.47 (m) and 7.58 (s), 7.7 to 8.5 (m), 8.96 (s), 9.07 (dd) and 9.13 (s) in the ratio 4:3:9:4:12.

Mass spectrum: molecular peak: 252, fragment masses: 237, 201, 192, 181, 126, 72.

EXAMPLE 2

(a) The procedure is as described in Example 1(a), but 50.5 g (0.2 mol) of 2,2-dimethyl-11-ethyl-11-aminoundeca-4,8-dienaldoxime, 25 g (0.245 mol) of acetic anhydride and, as the solvent, 100 ml of acetonitrile are used. After working-up, 37 g (0.159 mol) of 1,1-dimethyl-10-ethyl-10-amino-deca-3,7-diene-nitrile are obtained, corresponding to a yield of 79.5% of theory: boiling point: 84° C./1 Pa; $n_D^{20}$=1.4711. $^1$H NMR spectrum: $\tau$(ppm): 4.5 (m), 7.3 (m), 7.8 (m), 8.3–8.75 (m), 8.82 (s), 9.03 (t) in the ratio 4:1:8:8:2:3. Mass spectrum: molecular peak: 234, fragment masses: 205, 166, 82.

(b) The procedure is as described in Example 1(b), but 30 g (0.128 mol) of 1,1-dimethyl-10-ethyl-10-amino-deca-3,7-diene-nitrile, 100 ml of isopropanol, 23 g (1 mol) of sodium and 100 ml of xylene are used. After working-up, 22 g (0.925 mol) of 2,2-dimethyl-11-ethyl-1,11-diamino-undeca-4,8-diene are obtained, corresponding to a yield of 71.8% of theory; boiling point: 80° C./1 Pa; $n_D^{20}$=1.4809.

Analysis for $C_{15}H_{30}N_2$ (molecular weight 238.42): calculated: C, 75.57%; H, 12.69%; N, 11.75%. found: C, 75.7%; H, 12.5%; N, 10.7%.

$^1$H NMR spectrum: $\tau$(ppm): 4.6 (m), 7.3 (m), 7.56 (s), 7.7 to 8.2 (m), 8.6 (m) and 8.79 (s), 9.03 (t) and 9.12 (s) in the ratio 4:1:2:8:6:9.

Mass spectrum: molecular peak: 238, fragment masses: 223, 209, 181, 166, 126, 98.

EXAMPLE 3

(a) The procedure is as described in Example 1(a), but 473 g (1.65 mols) of 2-methyl-11-phenyl-11-amino-undeca-4,8-dienaldoxime, 169 g (1.65 mols) of acetic anhydride, 250 ml of acetic acid and excess HCl gas are used. After working-up, 160 g (0.6 mol) of 1-methyl-10-phenyl-10-amino-deca-3,7-diene-nitrile are obtained, corresponding to a yield of 36.4% of theory; boiling point: 135° C./1 Pa; $n_D^{20}$=1.5268. $^1$H NMR spectrum: $\tau$(ppm): 2.72 (s), 4.55 (m), 6.09 (t), 7.4 (m), 7.6 to 8.0 (m), 8.33 (s), 8.72 (d) in the ratio 5:4:1:1:8:2:3.

Mass spectrum: molecular peak: 268, fragment masses: 214, 146, 106, 79.

(b) The procedure is as described in Example 1(b), but 134 g (0.5 mol) of 1-methyl-10-phenyl-10-amino-deca-3,7-diene-nitrile, 58.5 g (2.54 mols) of sodium, 500 ml of toluene and 250 ml of isopropanol are used. After working-up, 60.5 g of (0.223 mol) of 2-methyl-11-phenyl-1,11-diamino-undeca-4,8-diene are obtained, corresponding to a yield of 44.5% of theory; boiling point: 103° C./13 Pa; $n_D^{20}$=1.5293.

Analysis for $C_{18}H_{28}N_2$ (molecular weight 272.44): calculated: C, 79.36%; H, 10.36%; N, 10.28%. found: C, 79.24%; H, 10.55%; N, 10.02%.

$^1$H NMR spectrum: $\tau$(ppm): 2.7 (m), 4.6 (m), 6.09 (t), 7.2–8.2 (m), 8.5 (m), 8.70 (s), 9.08 (d) in the ratio 5:4:1:10:1:4:3.

Mass spectrum: molecular peak: 272, fragment masses: 254, 167, 106, 79.

EXAMPLE 4

(a) The procedure is as described in Example 1(a), but 148 g (0.62 mol) of 2,11,11-trimethyl-11-amino-undeca-4,8-dienaldoxime, 63.3 g (0.62 mol) of acetic anhydride, 250 ml of acetic acid and excess HCl gas are used. After working-up, 87 g (0.396 mol) of 1,10,10-trimethyl-10-amino-deca-3,7-diene-nitrile are obtained, corresponding to a yield of 63.7% of theory; boiling point: 94° C./4 Pa; $n_D^{20}$=1.4706.

$^1$H NMR spectrum: $\tau$(ppm): 4.5 (m), 7.35 (sex), 7.6–8.1 (m), 8.38 (s), 8.68 (d), 8.88 (s) in the ratio 4:1:8:2:3:6.

Mass spectrum: molecular peak: 220, fragment masses: 205, 190, 178, 98, 58.

(b) The procedure is as described in Example 1(b), but 83 g (0.378 mol) of 1,10,10-trimethyl-10-amino-deca-3,7-diene-nitrile, 60 g (2.6 mols) of sodium, 500 ml of toluene and 250 ml of isopropanol are used. After working-up, 68 g (0.304 mol) of 2,11,11-trimethyl-1,11-diamino-undeca-4,8-diene are obtained, corresponding to a yield of 80.4% of theory; boiling point: 80° C./2 Pa; $n_D^{20}$=1.4785.

Analysis for $C_{14}H_{28}N_2$ (molecular weight 224.39): calculated: C, 74.94%; H, 12.58%; N, 12.49%. found: C, 74.72%; H, 12.84%; N, 12.34%.

$^1$H NMR spectrum: $\tau$(ppm): 4.6 (m), 7.42 (m), 7.9 (m), 8.5 (m), 8.88 (s), 9.07 (d) in the ratio 4:2:8:1:10:3.

Mass spectrum: molecular peak: 224, fragment masses: 209, 192, 167, 112, 96, 58.

EXAMPLE 5

(a) The procedure is as described in Example 1(a), but 150 g (0.59 mol) of 2,2,11,11-tetramethyl-11-amino-undeca-4,8-dienaldoxime, 75 g (0.735 mol) of acetic anhydride and 250 ml of glacial acetic acid are used. After working-up, 135 g (0.576 mol) of 1,1,10,10-tetramethyl-10-amino-deca-3,7-diene-nitrile are obtained, corresponding to a yield of 97.6% of theory; boiling point: 85° C./1 Pa.

(b) The procedure is as described in Example 1(b), but 50 g (0.213 mol) of 1,1,10,10-tetramethyl-10-amino-deca-3,7-diene-nitrile, 95 g (4.13 mols) of sodium, 500 ml of toluene and 300 ml of isopropanol are used. After working-up, 28.5 g (0.12 mol) of 2,2,11,11-tetramethyl- 1,11-diamino-undeca-4,8-diene are obtained, corresponding to a yield of 56.3% of theory; boiling point: 100° C./4 Pa; $n_D^{20} = 1.4772$.

Analysis for $C_{15}H_{30}N_2$ (molecular weight 238.42): calculated: C, 75.57%; H, 12.69%; N, 11.75%. found: C, 75.35%; H, 12.47%; N, 11.37%.

$^1$H NMR spectrum: $\tau$(ppm): 4.6 (m), 7.56 (s), 7.8 to 8.2 (m), 8.89 (s), 9.12 (s) in the ratio 4:2:8:10:6.

Mass spectrum: molecular peak: 238, fragment masses: 223, 206, 181, 126, 81, 58.

EXAMPLE 6

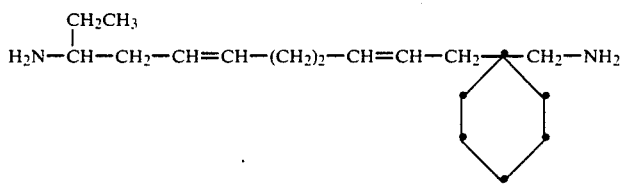

(a) 332 g (1.13 mols) of 2-pentamethylene-11-ethyl-11-amino-undeca-4,8-dienaldoxime are treated with 153 g (1.5 mols) of acetic anhydride, 90 g of glacial acetic acid and excess HCl gas, with stirring. The reaction mixture is heated for a further 4 hours under reflux, the glacial acetic acid is distilled off and the residue is dissolved in water. After the solution has been rendered basic with sodium hydroxide solution, the organic phase which separates out is taken up in toluene and the mixture is distilled. This gives 229 g (0.83 mol) of 1-pentamethylene-10-ethyl-10-amino-deca-3,7-diene-nitrile, corresponding to a yield of 73.8% of theory; boiling point: 138° C./1 Pa; $N_D^{20} = 1.4931$.

Analysis for $C_{18}H_{30}N_2$ (molecular weight 274.45): calculated: C, 78.77%; H, 11.02%; N, 10.21%. found: C, 78.67%; H, 10.83%; N, 9.98%.

$^1$H NMR spectrum: $\tau$(ppm): 4.6 (m), 7.4 (m), 7.8–8.9 (m), 9.1 (t) in the ratio 4:1:22:3.

Mass spectrum: molecular peak: 274, fragment masses: 259, 245, 191, 166, 112, 98.

(b) The procedure is as described in Example 1(b), but 65 g (0.237 mol) of 1-pentamethylene-10-ethyl-10-amino-deca-3,7-diene-nitrile, 48 g (2.08 mols) of sodium, 500 ml of toluene and 250 ml of isopropanol are used. After working-up, 43 g (0.153 mol) of 2-pentamethylene-11-ethyl-1,11-diamino-undeca-4,8-diene are obtained, corresponding to a yield of 64.5% of theory; boiling point: 140° C./3 Pa.

Analysis for $C_{18}H_{34}N_2$ (molecular weight 278.48): calculated: C, 77.63%; H, 12.31%; N, 10.06%. found: C, 78.20%; H, 12.29%; N, 9.73%.

$^1$H NMR spectrum: $\tau$(ppm): 4.6 (m), 7.35 (m) and 7.48 (s), 7.9 (m), 8.5 (m), 8.92 (s), 9.04 (t) in the ratio 4:3:8:12:4:3.

Mass spectrum: molecular peak 278, fragment masses 249, 221, 166, 152, 138, 112.

EXAMPLE 7

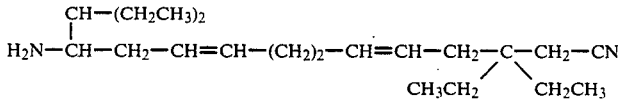

(a) The procedure is as described in Example 6(a), but 280 g (0.87 mol) 2,2-diethyl-11-(3-pentyl)-11-amino-undeca-4,8-dienaldoxime, 112 g (1.2 mols) of acetic anhydride, 75 g of glacial acetic acid and excess HCl gas are used. After working-up, 138 g (0.455 mol) of 1,1-diethyl-10-(3-pentyl)-10-amino-deca-3,7-diene-nitrile are obtained, corresponding to a yield of 52.3% of theory; boiling point: 139° C./3 Pa; $n_D^{20}$:1.4793.

Analysis for $C_{20}H_{36}N_2$ (molecular weight 304.52): calculated: C, 78.88%; H, 11.92%; N, 9.20%. found: C, 78.90%; H, 11.63%; N, 9.45%.

$^1$H NMR spectrum: $\tau$(ppm): 4.6 (m), 7.3 (m), 7.7–8.2 (m), 8.4–9.2 (m) in the ratio 4:1:8:23.

Mass spectrum: molecular peak 303, fragment masses: 275, 233, 142, 100, 82.

(b) The procedure is as described in Example 1(b), but 69.8 g (0.23 mol) of 1,1-diethyl-10-(3-pentyl)-10-amino-deca-3,7-diene-nitrile, 35 g (1.52 mols) of sodium, 250 ml of toluene and 70 ml of isopropanol are used. After working-up, 50 g (0.162 mol) of 2,2-diethyl-11-(3-pentyl)-1,11-diamino-undeca-4,8-diene are obtained, corresponding to a yield of 70.5% of theory; boiling point: 130° C./4 Pa; $n_D^{20}$: 1.4861.

Analysis for $C_{20}H_{40}N_2$ (molecular weight 308.55): calculated: C, 77.85%; H, 13.07; N, 9.08%. found: C, 77.92%; H, 13.31%; N, 8.94%.

$^1$H NMR spectrum: $\tau$(ppm): 4.6 (m), 7.25 (m), 7.57 (s), 7.7–8.8 (m), 9.02 (s) and 9.1 (m) in the ratio 4:1:2:17:16.

Mass spectrum: molecular peak 308, fragment masses: 279, 262, 237, 220, 209, 180, 154, 140, 126, 100.

(B) USE EXAMPLES

EXAMPLE I 62.8 g of 2,2-dimethyl-11-isopropyl-1,11-diamino-undeca-4,8-diene, 36.4 g of adipic acid, 0.25 ml of a 10% aqueous $NH_4H_2PO_2$ solution and 0.5 g of di-tert.butyl-p-cresol are pre-condensed in an autoclave for 90 minutes, in a nitrogen atmosphere, then condensed further for 4 hours in an open polycondensation vessel, in a stream of nitrogen, and finally post-condensed for 1 hour in a high vacuum. All polycondensation steps are carried out at 250° C.

Elementary analysis of the polyamide obtained: calculated: C, 72.88%; H, 10.57%; N, 7.73%. found: C, 70.20%; H, 10.47%; N, 7.45%.

Content of end groups: —COOH: 0.16 milliequivalent/g; —NH$_2$: 0.04 milliequivalent/g.

Glass transition temperature Tg: 45° C. [determined in a differential scanning calorimeter (DSC)]; reduced viscosity (0.5% solution of m-cresol at 25° C.) $\eta$ red = 0.70 dl/g.

EXAMPLE II (a) Preparation of a salt of terephthalic acid (TPA) and 2,2-dimethyl-11-isopropyl-1,11-diamino-undeca-4,8-diene (undecadiene-diamine=UDD)

97.1 g of terephthalic acid are suspended in 2,400 ml of water and 600 ml of methanol. 148.9 g of UDD are added dropwise to the resulting suspension, at the reflux temperature, a homogeneous solution being formed. After boiling for 60 minutes, the solution is left to cool to 0°–5° C. After 24 hours, the salt formed is filtered off and dried at 80° C. in vacuo. Yield: 180 g (73.6% of theory).

(b) Preparation of a salt of adipic acid (AA) and UDD:

36.2 g of adipic acid are dissolved in 270 ml of absolute ethanol at 50° C. After the solution has cooled, 69.7 g of UDD in 107 ml of absolute ethanol are added. The salt, which precipitates after two thirds of the solvent has been stripped off and the remainder has been cooled to 0°–5° C., is filtered off and dried in vacuo at 20° C. Yield: 82.5 g (85.3% of theory).

56.0 g of the salt of TPA and UDD obtained according to a), and 14.0 g of the above salt of adipic acid and UDD, are subjected to polycondensation as described in Example I, but the last condensation step in vacuo is omitted. Glass transition temperature of the polyamide=105° C., $\eta$ red (0.5% solution in m-cresol at 25° C.)=0.72 dl/g.

EXAMPLE III

A 10% solution in chloroform/ethanol (1:1) of the polyamide prepared according to Example I, which contains 5% by weight of cumene hydroperoxide, is coated with the aid of a 50 μm blade onto a copper printed circuit. The coating is dried for 3 minutes at 100° C., after which the layer thickness is about 5 μm. Subsequent hardening at 150° C. for 90 minutes in a nitrogen atmosphere gives a hard, transparent and shiny layer with good adhesion to the copper. If the circuit board treated in this way is left to stand for 72 hours in chloroform at 60° C., the polyamide is not dissolved and the adhesion of the polyamide is sufficient to prevent etching of the underlying copper. After storage for one week in water at 20° C., the coating retains its transparency and good adhesion to the copper; the water uptake is less than 1% by weight.

EXAMPLE IV (1) 2.5 g of the polyamide obtained according to Example I, 1.5 g of pentaerythritol tetrakis-(3-mercaptopropionate) and 95 mg of thioxanthone are dissolved in 10.8 ml of chloroform and the solution is applied with a 50 μm blade to a 100 μm thick polyester film. The coating is dried for 3 minutes at 100° C. and exposed with a 5,000 W high-pressure mercury lamp through a photographic mask for 15 seconds (distance of the high-pressure mercury lamp from the vacuum table: 70 cm). After developing for 30 seconds in chloroform, a well-resolved negative relief image is obtained.

(ii) The process described under (i) is repeated using 81.6 mg of benzophenone in place of the thioxanthone and using an exposure time of 60 seconds.

| Experiment | Exposure time (seconds) | Last step of which an image is formed on a 21 step sensitivity guide from the Stouffer Company |
|---|---|---|
| (i) | 15 | 8 |
| (ii) | 60 | 8 |

What is claimed is:

1. A compound of the formula I

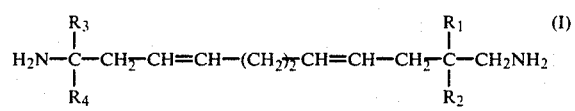

in which $R_1$ is alkyl having 1–12 C atoms, $R_2$ is hydrogen or alkyl having 1–12 C atoms, $R_3$ is alkyl having 1–12 C atoms, cycloalkyl having 4–12 ring C atoms, aralkyl having 7 or 8 C atoms, substituted or unsubstituted aryl or, if $R_4$ is hydrogen, is also —CH=CH—alkyl or —C(alkyl)=CH—alkyl each having 1–4 C atoms in the alkyl groups, and $R_4$ is hydrogen, alkyl having 1–12 C atoms, cycloalkyl having 4–12 ring C atoms, aralkyl having 7 or 8 C atoms or substituted or unsubstituted aryl, or $R_1$ and $R_2$ and/or $R_3$ and $R_4$ together are alkylene having 3–11 C atoms.

2. A compound of the formula I according to claim 1 in which $R_1$ is alkyl having 1–5 C atoms, $R_2$ is hydrogen or alkyl having 1–5 C atoms, or $R_1$ and $R_2$ together are alkylene having 4–7 C atoms, $R_3$ is alkyl having 1–7 C atoms, cycloalkyl having 5–8 C atoms, unsubstituted phenyl or, if $R_4$=H, is also —C($C_2H_5$)=CH—$CH_3$, and $R_4$ is hydrogen or alkyl having 1–5 C atoms.

3. A compound of the formula I according to claim 2 in which $R_3$ is alkyl having 1–5 C atoms, unsubstituted phenyl or, if $R_4$=H, is also —C($C_2H_5$)=CH—$CH_3$, and $R_4$ is hydrogen or methyl.

4. A compound of the formula I according to claim 1 in which $R_1$ is methyl or ethyl, $R_2$ is hydrogen, methyl or ethyl, $R_3$ is alkyl having 1–5 C atoms or unsubstituted phenyl, and $R_4$ is hydrogen or methyl.

5. The compound of the formula I according to claim 1 in which $R_1$ and $R_2$ are methyl, $R_3$ is isopropyl and $R_4$ is hydrogen.

* * * * *